(12) United States Patent
Carter

(10) Patent No.: US 6,799,575 B1
(45) Date of Patent: Oct. 5, 2004

(54) CANNULA FOR THE SEPARATION OF INHALED AND EXHALED GASES

(76) Inventor: Aaron Carter, 2000 Vassar St., P.O. Box 10837, Reno, NV (US) 89510

( * ) Notice: Subject to any disclaimer, the term of this patent is extended or adjusted under 35 U.S.C. 154(b) by 166 days.

(21) Appl. No.: 10/127,166

(22) Filed: Apr. 20, 2002

Related U.S. Application Data

(60) Provisional application No. 60/285,480, filed on Apr. 21, 2001.

(51) Int. Cl.[7] .............................................. A61M 15/08
(52) U.S. Cl. .............. 128/207.18; 600/532; 128/204.18
(58) Field of Search ........................ 128/200.14, 200.24, 128/203.22, 207.18, 206.11, 204.18; 600/529, 532, 538, 543; 604/94.01

(56) References Cited

U.S. PATENT DOCUMENTS

| | | | | |
|---|---|---|---|---|
| 5,046,491 A | * | 9/1991 | Derrick .................. | 128/200.24 |
| 5,335,656 A | | 8/1994 | Bowe et al. | |
| 6,422,240 B1 | * | 7/2002 | Levitsky et al. ....... | 128/207.18 |
| 6,439,234 B1 | * | 8/2002 | Curti et al. ............. | 128/207.18 |
| 2002/0112730 A1 | * | 8/2002 | Dutkiewicz ............ | 128/207.18 |

FOREIGN PATENT DOCUMENTS

JP     3-57460    * 7/1989 ............ 128/207.18

OTHER PUBLICATIONS

63:572–573, 1985, Ibarra, Lees.
65:565–566, 1986, Huntington, King.
64:664, 1986, Norman, Zeig, Ahmad.

* cited by examiner

*Primary Examiner*—Glenn K. Dawson

(57) ABSTRACT

An improved nasal cannula for isolating, monitoring and measuring the content of a patients exhaled gases. The cannula includes an integral connector that is attached to the wall of a hollow nare to create a gas-tight interface. The other end of the connector is attached to tubing that forms an integral seal with the cannula port to create a continuous, gas-tight flow channel that is separated from the hollow cannula body. The integral connector provides a direct, isolated flow channel that eliminates the undesirable dead space in which exhaled gases from a patient can be entrapped and stagnate, resulting in cross contamination.

5 Claims, 1 Drawing Sheet

CANNULA FOR THE SEPARATION OF INHALED AND EXHALED GASES

CROSS-REFERENCE TO RELATED APPLICATIONS

This application is entitled to the benefit of Provisional Patent Application No. 60/285,480, filed Apr. 21, 2001.

TECHNICAL FIELD OF THE INVENTION

This invention relates to the analysis, diagnosis and medical treatment of patients, specifically to an improved cannula for isolating, monitoring and measuring exhaled gases that are separated from inhaled gases.

DESCRIPTION OF PRIOR ART

Patients who are ill or undergoing various surgical procedures are often times given oxygen, anesthetic or other treating gases. In many cases, it is desirable and necessary that oxygen or anesthetic be supplied to the patient while simultaneously measuring at least one component (such as carbon dioxide) of the patients exhaled gas. An accurate measurement of the components of the exhalation gases (including end-tidal carbon dioxide) while the patient is undergoing a medical procedure (in intensive care or recovery situations) provides critical feedback for quickly analyzing body functions and prescribing proper treatment.

Previously, attempts were made to measure at least one component of a patient's exhaled gas from samples diluted by the oxygen treating gas. The apparatus for administering the treating gas did not provide adequate isolation or separation between the treating gas and the patient's exhalation gases. This caused inaccuracies and resulted in poor correlations between the measured amount of carbon dioxide and the actual amount of carbon dioxide in the patients blood stream.

A number of researchers (including Iberia, et al.; Norman, et al.; Huntington, et al.) Have published technical papers (ex., journal Anesthesiology) addressing this problem. Their approaches, which attempted to measure at least one component of a patients exhalation gas while simultaneously administering a treating gas (oxygen) included extracting gas samples from a patient's oxygen mask. The results from these approaches did not give accurate correlations between a patient's level of carbon dioxide measured from exhaled gas and the measured levels of carbon dioxide in the patient's blood stream.

This problem has been partially solved by Bowe et al. (U.S. Pat. No. 5,335,656, Aug. 9, 1994), but this apparatus still has some significant disadvantages. Bowe et al. described a cannula that uses a wall member located between two hollow nasal prongs to provide a gas tight seal that defines separate inhalation and exhalation manifolds. While this cannula provides separation between the treating gas (typically oxygen) and the patient's exhalation gases (targeted CO2 sampling components), it also creates an undesirable dead space in which a patients exhaled gases can be entrapped and stagnate. This dead space becomes a potential and likely source for cross contamination between a patient's current and previously exhaled gases. Whereby, inaccuracies can be introduced into the patients measured levels of exhaled end-tidal carbon dioxide. These inaccuracies can inhibit detection of minute changes in a patient's body functions, which is critical in intensive care situations. In addition, the wall member located midway between the cannula nasal will reduce the elasticity and flexibility of the cannula body and possibility cause or contribute to patient discomfort.

An alternative cannula is also described by Bowe et al., which eliminates the dead space created from locating a wall member in the cannula body, midway between the nasal prongs. This alternative cannula entails modifying a conventional nasal cannula by cutting or piercing an aperture in the main body of the cannula at the base of one of the nasal prongs. A nozzle-like piece that is substantially more rigid than the cannula material is then inserted through the aperture and into the corresponding nasal prong to form a separate flow channel for gas. This alternative cannula is cumbersome and would require a difficult, time consuming and costly process to manufacture. The alternative cannula configuration would also make it difficult to avoid passing the flexible tubing over the mouth or eyes of a patient when connecting to a source of treating gas or an analyzer. In addition, since the rigid nozzle-like piece is inserted into the cannula's nasal prong, which will be placed in a patient's sensitive nasal cavity, it can cause or contribute to irritation and significant patient discomfort.

SUMMARY OF THE INVENTION

The improved cannula of the present invention eliminates the problems of the prior-art by providing a continuous, completely isolated flow channel that eliminates the undesirable dead space in which a patients exhaled gases can be entrapped, stagnate and result in cross contamination. Hence, the cannula of the present invention enables more accurate analyses and measurements of a patient's exhaled gas, while minimizing discomfort.

OBJECTS AND ADVANTAGES

Accordingly, several objects and advantages of the present invention are:

(a) to provide a cannula that improves the accuracy of the quantitative measurements of a patients exhaled gas;

(b) to provide a cannula that gives a better correlation between the measurements of a patients exhaled gaseous components and the patients actual arterial blood samples;

(c) to provide a cannula that eliminates the undesirable dead space in which a patients exhaled gases can be entrapped and stagnate, resulting in cross contamination;

(d) to provide a cannula with an isolated flow channel that eliminates the potential for a patients exhaled gases to re-breathe, mix or re-circulate, thereby causing contamination;

(e) to provide a cannula that minimizes patient discomfort.

Further objects and advantages are to provide an invention that can be easily and cost effectively manufactured and used with a conventional cannula, manifold, or other components. Still further objects and advantages will become apparent from a consideration of the ensuing description and drawings.

| REFERENCE NUMERIALS IN DRAWINGS | | | |
|---|---|---|---|
| 20 | nasal cannula body | 22 | nasal nare |
| 24 | nasal nare | 25 | hollow cannula body |
| 26 | tubing | 27 | cannula port |
| 28 | tubing | 29 | cannula port |
| 30 | flexible connector | 32 | tubing end |
| 34 | tubing end | 36 | connector end |
| 38 | seal | 40 | nare/seal interface |
| 42 | formed connector | 44 | formed connector |
| 46 | nare/connector interface | | |

DESCRIPTION OF PREFERRED AND OTHER EMBODIMENTS

Figure 1:
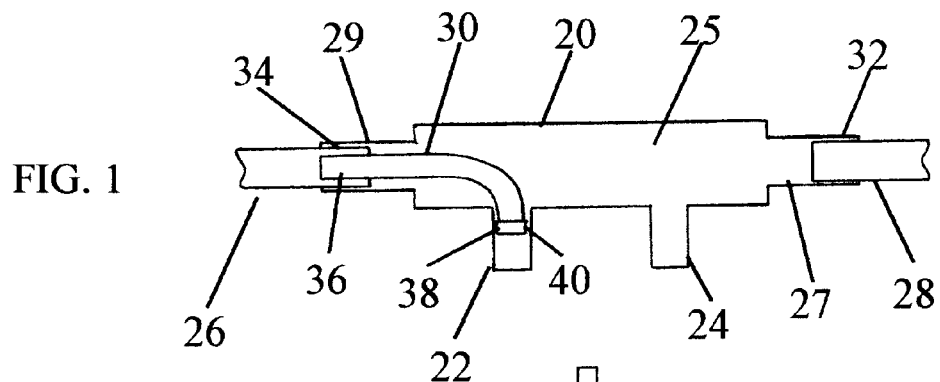
FIG. 1 is a plan view of a conventional nasal cannula modified in accordance with the invention.

FIGS. 1–4 illustrate how a conventional cannula may be modified using the present invention, to create a cannula that eliminates the undesirable dead space and provide a direct, isolated flow channel through which a patients exhaled gases pass uncontaminated, facilitating more accurate measurements. FIG. 1 shows a plan view of a conventional nasal cannula 20 with a preferred embodiment of a flexible connector 30 with a seal 38. The cannula 20 consists of a hollow body 25 with two hollow nasal nares 22 and 24, which are designed to fit into the nasal passage of a patient. The cannula body 20 may be formed or molded from flexible plastic or other material. The entire cannula body 20 is preferably made from a flexible plastic material with elastic properties.

Figure 2:
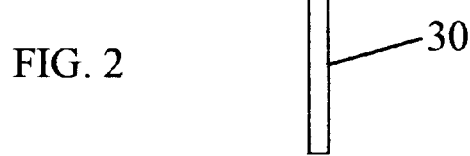
FIG. 2 shows a flexible connector in its un-deformed shape.
Figure 3:
FIG. 3 shows a seal that gets attached to or is an integral part of the connector and/or the cannula nasal nare.
Figure 4:
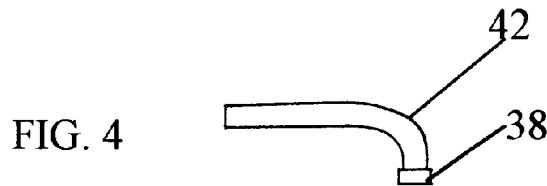
FIG. 4 shows a flexible, rigid or semi-rigid connector formed to fit inside the cannula body and searingly attach to the cannula nasal nare.

The flexible connector 30 shown in FIG. 2 is a hollow tube and its dimensions are dependent on the design of the nasal nare 22 and cannula port 29. The outside diameter of the flexible connector 30 is typically dependent on the inside diameter of the hollow nasal nare 22. The flexible connector 30 may be made from flexible plastic or other material. The seal 38 shown in FIG. 3 is hollow and its dimensions are dependent on the outside diameter of the flexible connector 30 and the inside diameter and length of the hollow nare 22. The seal 38 may be made from flexible plastic or other material. FIG. 4 shows an additional embodiment of a formed connector 42 that is made to fit inside of the hollow cannula body 25, the nasal nare 22, and the cannula port 29. The formed connector 42 is a hollow tube with its bend radius and dimensions dependent on the design of the cannula body 20, the nasal nare 22, and the cannula port 29. The outside diameter of the formed connector 42 is typically dependent on the inside diameter of the hollow nare 22. The formed connector 42 may be made from flexible, semi-rigid, rigid or other material.

One end of the flexible connector 30 is inserted inside of the seal 38. The flexible connector 30 preferably has a larger outside diameter than the seal 38, such that the outside surface of the flexible connector 30 is compressed and the resulting radial pressure forms a continuous gas tight interface between the outside surface of the flexible connector 30 and the inside surface of the seal 38. The necessary sealing between the flexible connector 30 and the seal 38 may also be accomplished by some other form of adhesion, such as adhesive compounds, solvents or sonic welds. The end 36 of the flexible connector 30 without the attached seal 38 is inserted into the nasal nare 22, pushed through the nare 22, into the hollow cannula body 25, and bent such that it exits the cannula port 29. The end of the flexible connector 30 with the attached seal 38 is positioned in the nare 22 and forms a nare/seal interface 40. The attached seal 38 preferably has a larger outside diameter than the inside diameter of the nare 22, such that the outside surface of the seal 38 is compressed and the resulting radial pressure forms a continuous gas tight interface between the outside surface of the seal 38 and the inside surface of the nare 22. The necessary sealing between the attached seal 38 and the nasal nare 22 may also be accomplished by some other form of adhesion, such as adhesive compounds, solvents or sonic welds.

The connector end 36 is attached to the tubing end 34. The tubing 26 may be made from flexible plastic or other material, with dimensions that are dependent on the diameter of the connector end 36 and the design of the cannula port 29. The connector end 36 is preferably inserted into the inside diameter of the hollow tubing end 34. The hollow tubing end 34 also inserts into the inside diameter of the cannula port 29, to create a continuous gas-tight flow channel that is sealed and isolated from the hollow cannula body 25. The necessary sealing between the mating surfaces of the connector end 36 and the inside diameter of the tubing end 34; and the outside diameter of the tubing end 34 and the inside diameter of the cannula port 29; may be accomplished by various means, such as adhesive compounds, solvents, or sonic welds.

Referring again to FIG. 4, an additional embodiment of a formed connector 42, the end with the bend radius may be inserted inside of the seal 38. The formed connector 42 preferably has a larger outside diameter than the seal 38, such that the outside surface of the formed connector 42 is compressed and the resulting radial pressure forms a continuous gas tight interface between the outside surface of the formed connector 42 and the inside surface of the seal 38. The necessary sealing between the formed connector 42 and the seal 38 may also be accomplished by some other form of adhesion, such as adhesive compounds, solvents or sonic welds. The formed connector 42 may be inserted through the nasal nare 22 or the cannula port 29, into the hollow cannula body 25. The end of the formed connector 42 with the attached seal 38 is positioned in the nare 22 and forms a nare/seal interface 40. The attached seal 38 preferably has a larger outside diameter than the inside diameter of the nare/seal interface 40, such that the outside surface of the seal 38 is compressed and the resulting radial pressure forms a continuous gas tight interface between the outside surface of the seal 38 and the inside surface of the nare 22. The necessary sealing between the attached seal 38 and the nasal nare 22 may also be accomplished by some other form of adhesion, such as adhesive compounds, solvents or sonic welds.

As previously shown, the connector end 36 of the formed connector 42 is preferably inserted into the inside diameter of the hollow tubing end 34. The hollow tubing end 34 also inserts into the inside diameter of the cannula port 29, to create a continuous gas-tight flow channel that is sealed and isolated from the hollow cannula body 25. The necessary sealing between the mating surfaces of the connector end 36 and the inside diameter of the tubing end 34; and the outside diameter of the tubing end 34 and the inside diameter of the cannula port 29; may be accomplished by various means, such as adhesive compounds, solvents, or sonic welds.

Figure 5:
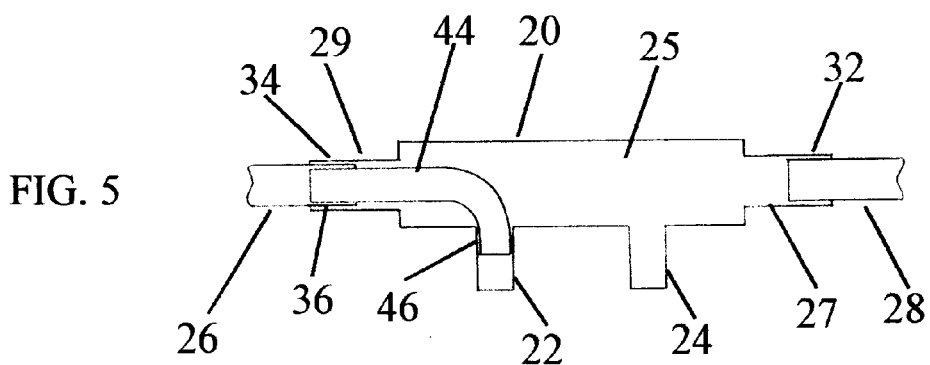
FIG. 5 is a plan view of a conventional nasal cannula with an alternative connector in accordance with the invention.
Figure 6:
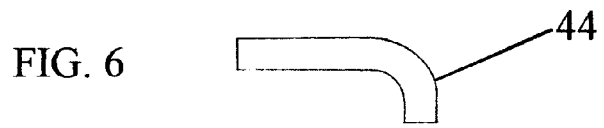
FIG. 6 shows a formed flexible, semi-rigid or rigid integral connector that fits inside the cannula body and searingly attaches to the cannula nasal nare.

FIG. 5 shows a plan view of a conventional nasal cannula 20 that is identical to FIG. 1, except for an alternate embodiment of a formed connector 44. FIG. 6 shows an alternate embodiment of a formed connector 44 that is made to fit inside of the hollow cannula body 25, the nasal nacre 22, and the cannula port 29. The formed connector 44 is a hollow tube with its bend radius and dimensions dependent on the design of the cannula body 20, the nasal nare 22, and the cannula port 29. The outside diameter of the formed connector 44 is typically dependent on the inside diameter of the hollow nare 22. The formed connector 44 may be made from flexible, semi-rigid, rigid or other material.

The formed connector 44 preferably has a larger outside diameter than the nare/connector interface 46, such that the outside surface of the formed connector 44 is compressed and the resulting radial pressure forms a continuous gas tight interface between the outside surface of the formed connector 44 and the inside surface of the nasal nacre 22. The necessary sealing between the formed connector 44 and the nacre 22 may also be accomplished by some other form of adhesion, such as adhesive compounds, solvents or sonic welds. The formed connector 44 may be inserted through the nasal nare 22 or the cannula port 29, into the hollow cannula body 25. The end of the formed connector 44 With the bend is positioned in the nare 22 and forms a nare/connector interface 46. As previously shown, the connector end 36 of the formed connector 44 is inserted into the hollow tubing end 34, which also inserts into the inside diameter of the cannula port 29, to create a continuous gas-tight flow channel that is sealed and isolated from the hollow cannula body 25.

Additional embodiments for the interfaces may take various forms such as attaching a seal 38 to the connector end 36 or the cannula port 29; sizing the cannula port 29, tubing end 34 and connector end 36 such that mating surfaces are formed; transitioning or stepping down the diameter of the nasal nare 22 to create an integral seal with the connector 30/42/44, etc. These various interfaces may suggest other forms to those skilled in the art. The flexible connector 30 and formed connector 42/44 may have various shapes, angles and bend radii, which may suggest other geometries to those skilled in the art. The nasal cannula 20 may have various shapes, sizes, and forms, including manifolds and non-conventional cannula, which may suggest other geometries or designs to those skilled in the art.

OPERATION OF INVENTION

FIG. 1 and FIG. 5 show a nasal cannula 20 consisting of a hollow body with two hollow nasal nares 22 and 24, which are designed to fit into the nasal passage of a patient. A flexible connector 30 or formed connector 42/44 is attached to the wall of the hollow nare 22 and the tubing end 34 to create a continuous gas-tight flow channel that is sealed and isolated from the hollow cannula body 25. The connector 30/42/44 provides a direct, isolated flow channel with no dead space, through which a patients exhalation gases pass uncontaminated.

The flexible tubing 26 may be connected to a breathing gas analyzer or other systems for monitoring and measuring a patients exhaled gases. The nasal nare 22 withdraws a patients exhaled gases, typically carbon dioxide, through the connector 30/42/44 and tube 26, to a breathing gas analyzer. The tubing end 32 of the tubing 28, is attached to the cannula port 27 to form a sealed inhalation manifold. The tubing 28 may be connected to an oxygen flow-regulating device. The nasal nare 24 supplies oxygen to a patient from the oxygen source.

CONCLUSIONS, RAMIFICATIONS AND SCOPE OF INVENTION

The reader will see that the improved cannula of the present invention eliminates the undesirable dead space in which a patients exhaled gases can be entrapped and stagnate, resulting in cross contamination. Accordingly, the cannula of the present invention enables more accurate quantitative measurements of a patients exhaled gases, which are critical when monitoring a patients body functions in intensive care situations. In addition, the present invention has the following advantages:

it provides an isolated flow channel that eliminates the potential for a patients exhaled gases to re-breathe, mix or re-circulate, thereby causing contamination;

it increases the probability of a better correlation between the measurements of a patients exhaled gaseous components and the patients actual arterial blood samples;

it provides a cannula that minimizes patient discomfort;

it provides a cannula that is simple and cost effective to manufacture.

Although the description above contains many specificities, these should not be construed as limiting the scope of the present invention but as merely providing illustrations of some of the preferred embodiments of this invention. For example, the interfaces may take various forms such as attaching a seal to the connector end or cannula port; sizing the cannula port, tubing end and connector end such that mating surfaces are formed; or stepping down the diameter of the nasal nare to create an integral seal with the formed connector, etc. The flexible or formed connector may have various shapes, angles and bend radii, etc. The nasal cannula may have various shapes, sizes, or forms, including manifolds and non-conventional cannula, etc. These alternate embodiments may suggest still other forms to those skilled in the art.

Thus the scope of the invention should be determined by the appended claims and their legal equivalents, rather than by the examples given.

I claim:

1. A nasal cannula for administering treating gases to a patient that eliminates the dead space through which a patients exhalation gases pass, and provides a direct, isolated flow channel, comprising:

(a) a hollow body with two hollow nasal nares that are designed to fit into the nasal passage of a patient;

(b) a connector with one end attached to a wall of one of said hollow nasal nares and the other end of said connector attached to tubing which attaches to an exhalation port of said hollow body, whereby creating a flow channel that is sealed and isolated from said hollow body;

(c) said hollow body also having an inhalation port with a means for connecting tubing to a source of treating gas, and having an exhalation port with a means for connecting tubing to a monitoring device.

2. The nasal cannula of claim 1 wherein said connector attaches to the wall of said nasal nare to form a gas-tight interface.

3. The nasal cannula of claim 1 wherein said connector attaches to said tubing that attaches to said exhalation port to form a gas-tight interface.

4. The nasal cannula of claim 1 wherein the first of said two nasal nares is supplied with said patients treating gas.

5. The nasal cannula of claim 1 wherein the second of said two nasal nares discharges said patient's exhalation gases directly through said connector.

* * * * *